United States Patent [19]

Grieder et al.

[11] 4,260,782
[45] Apr. 7, 1981

[54] PROCESS FOR THE PREPARATION OF N-(1'-ALKOXYCARBONYLETHYL)-2,6-DIALKYLANILINES

[75] Inventors: Alfred Grieder, Böckten; Klaus-Jürgen Coers, Reinach, both of Switzerland

[73] Assignee: Ciba-Geigy Corporation, Ardsley, N.Y.

[21] Appl. No.: 157,761

[22] Filed: Jun. 9, 1980

[51] Int. Cl.³ ............................................. C07C 101/44
[52] U.S. Cl. .................................................... 560/43
[58] Field of Search ........................................ 560/43

[56] References Cited

U.S. PATENT DOCUMENTS

| Re. 29,468 | 11/1977 | Clayton | 560/43 |
| 2,273,556 | 2/1942 | Bean | 560/43 |
| 3,402,198 | 9/1968 | Bolhofer | 560/43 X |
| 3,882,162 | 5/1975 | Clayton | 560/43 |
| 4,008,066 | 2/1977 | Moser | 71/76 |
| 4,025,648 | 5/1977 | Hubele | 560/43X |
| 4,032,657 | 6/1977 | Moser | 560/43 X |

FOREIGN PATENT DOCUMENTS 572017   1/1976   Switzerland .

*Primary Examiner*—Paul F. Shaver
*Attorney, Agent, or Firm*—Karl F. Jorda

[57] ABSTRACT

A process is described for the preparation of N-(1'-alkoxycarbonylethyl)-2,6-dialkylanilines of the formula

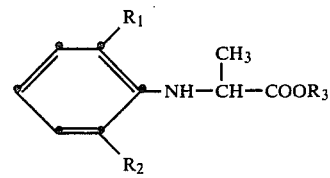

in which $R_1$ and $R_2$ are each methyl or ethyl and $R_3$ is an alkyl group having 1–4 carbon atoms. According to this process, a 2-chloropropionic acid ester having 1–4 carbon atoms in the alkyl group is reacted in the presence of water and of a quaternary ammonium or phosphonium salt with an alkali metal iodide to give a mixture of the 2-chloropropionic acid ester and the 2-iodopropionic acid ester, and this mixture is subsequently reacted, after separating off the aqueous phase, at 110–130° C., in the presence of an alkali metal carbonate or alkali metal bicarbonate as an acid-binding agent, with excess 2,6-dialkylaniline, the reaction mixture is extracted with water and the mixture of the 2,6-dialkylaniline of the formula IV and the N-(1'-alkoxycarbonylethyl)-2,6-dialkylaniline of the formula I, which is obtained after separating off the aqueous extract, is separated by distillation. The N-(1'-alkoxycarbonylethyl)-2,6-dialkylanilines of the above formula which can be prepared by this process are valuable intermediates for the preparation of compounds having a pesticidal action.

16 Claims, No Drawings

PROCESS FOR THE PREPARATION OF N-(1'-ALKOXYCARBONYLETHYL)-2,6-DIALKYLANILINES

The present invention relates to a process for the preparation of N-(1'-alkoxycarbonylethyl)-2,6-dialkylanilines of the formula I

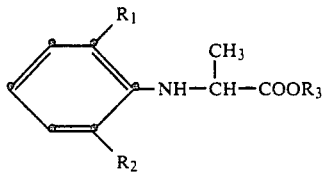

in which $R_1$ and $R_2$ are each methyl or ethyl and $R_3$ is an alkyl group having 1-4 carbon atoms.

The N-(1'-alkoxycarbonylethyl)-2,6-dialkylanilines of the formula I are valuable intermediates for the preparation of compounds having a pesticidal action. They can, for example, be converted by reaction with acid chlorides, such as chloroacetyl chloride, methoxyacetyl chloride or furan-2-carboxylic acid chloride, into corresponding N-acylanilines, which are distinguished by an outstanding action against phytopathogenic microorganisms and therefore find extensive use in plant protection. N-Acylanilines of this type, and also their preparation and use, are described, for example, in U.S. Pat. Nos. 4,008,066, 4,094,990 and 4,151,299.

Particularly preferred N-acylanilines of the abovementioned type, which can be prepared by acylation of the N-(1'-alkoxycarbonylethyl)-2,6-dialkylanilines of the formula I which can be prepared according to the invention, are N-methoxyacetyl-N-(1'-methoxycarbonyl ethyl)-2,6-dimethylaniline and N-(2''-furoyl)-N-(1'-methoxycarbonylethyl)-2,6-dimethylaniline.

It is known to prepare N-(1'-alkoxycarbonylethyl)-2,6-dialkylanilines by reacting 2,6-dialkylanilines with α-halogenopropionic acid esters. This reaction is problematical on the one hand because of steric hindrance due to the alkyl groups in the ortho-position and on the other hand because of the sensitivity of the α-halogenopropionic acid esters to hydrolysis. Various proposals have already been made for solving the problems associated with carrying out this process.

Thus, U.S. Pat. No. 3,882,162 mentions the reaction of α-halogenoacetic acid esters and 2,6-dialkylanilines in the presence of aqueous alkali metal hydroxides. Because of side reactions, such as N,N-dialkylation and hydrolysis of the ester group, the desired products are obtained only in inadequate purity and in unsatisfactory yields by this method.

U.S. Pat. No. 3,882,162 proposes avoiding the disadvantages associated with the abovementioned process by carrying out the reaction of the 2,6-dialkylaniline with the α-halogenocarboxylic acid ester in the presence of excess 2,6-dialkylaniline, as an acid-binding agent, and in the presence of a catalytic amount of the hydrochloride of the particular 2,6-dialkylaniline, at temperatures of 100°-250° C. However, with this process also, the yields achievable are below 70% of theory.

Furthermore, it is proposed in Swiss Pat. No. 572,017 to react anilines substituted in the nucleus, at temperatures of 100°-175° C., in the presence of a tertiary amine as an acid-binding agent, with α-halogenocarboxylic acid esters, and, according to a preferred embodiment of this process, the reaction is carried out in excess ester as the solvent and, in order to accelerate the reaction, the tertiary amine is already added in the form of a salt, for example in the form of the hydrochloride, at the start of the reaction. With this process, aniline conversions of 90–96%, a selectivity of 78–90% and yields of N-(1'-alkoxycarbonylalkyl)-anilines of 70–86% of theory are obtained; the yields quoted are based not on the pure product actually isolated, but on an analytical determination of the content of pure product in the crude product.

Furthermore, the reaction of 2,6-dimethylaniline at 120°-125° C., in the presence of sodium bicarbonate as an acid-binding agent, with a three-fold molar excess of methyl 2-bromopropionate has been disclosed in U.S. Pat. No. 4,008,066. With this process, N-(1'-methoxycarbonylethyl)-2,6-dimethylaniline is obtained in a yield of 79.6% of theory.

As is shown by the above survey of the prior art, it is not possible with the processes disclosed hitherto to prepare N-(1'-alkoxycarbonylethyl)-2,6-dialkylanilines in satisfactory yield and purity. It is, therefore, the object of the present invention to provide a process which avoids the disadvantages of the known processes and which enables N-(1'-alkoxycarbonylethyl)-2,6-dialkylanilines of the formula I to be prepared in satisfactory yield and purity in a simple manner.

According to the present invention, it is proposed to prepare the N-(1'-alkoxycarbonylethyl)-2,6-dialkylanilines of the formula I by reacting a 2-chloropropionic acid ester of the formula II

in which $R_3$ is as defined under formula I, in the presence of water and of a quaternary compound of the formula III

in which Q is nitrogen or phosphorus, the radicals $R_4$, $R_5$, $R_6$ and $R_7$ are each an alkyl radical having 1 to 16 carbon atoms, or phenyl, and one of the radicals $R_4$, $R_5$, $R_6$ and $R_7$ can also be benzyl, and, if Q is nitrogen, Q together with three of the radicals $R_4$, $R_5$, $R_6$ and $R_7$ can also be a pyridine radical, whilst the fourth radical is alkyl having 1-16 carbon atoms, phenyl or benzyl, and $X^\ominus$ is a halide anion or a bisulfate anion, with an alkali metal iodide, to give a mixture of the 2-chloropropionic acid ester and the corresponding 2-iodopropionic acid ester, and subsequently reacting this mixture, after separating off the aqueous phase, at 110°-130° C. with excess 2,6-dialkylaniline of the formula

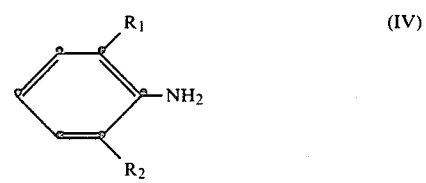

in which $R_1$ and $R_2$ are as defined under formula I, extracting the reaction mixture with water and separating, by distillation, the mixture of N-(1'-alkoxycarbonylethyl)-2,6-dialkylaniline of the formula I and 2,6-dialkylaniline of the formula IV, which is obtained after separating off the aqueous extract.

Suitable alkali metal iodides, which are reacted with the 2-chloropropionic acid ester of the formula II to give a mixture of the 2-chloropropionic acid ester and the 2-iodopropionic acid ester, are lithium iodide, sodium iodide, potassium iodide, rubidium iodide and caesium iodide. Sodium iodide and potassium iodide are preferably used. The alkali metal iodide can as a rule be employed in an amount of 0.3–0.6 mol per mole of 2-chloropropionic acid ester of the formula II, so that an ester mixture is obtained which consists to the extent of 40–70 mol % of 2-chloropropionic acid ester and to the extent of 30–60 mol % of 2-iodopropionic acid ester. Preferably 0.45–0.55 mol of alkali metal iodide is used per mol of 2-chloropropionic acid ester of the formula II, so that an ester mixture results which consists of 2-chloropropionic acid ester and 2-iodopropionic acid ester, each to the extent of about 50 mol %. The reaction is carried out in the presence of water. As a rule, water is used in an amount such that the reaction mixture consists to the extent of about 40–50 percent by weight of water.

According to the invention, the quaternary compounds of the formula III can be used in an amount of 0.5–5% by weight, based on the 2-chloropropionic acid ester of the formula II employed. Preferably, 1–3% by weight of quaternary compounds of the formula III are used, based on the 2-chloropropionic acid ester of the formula II employed.

Examples of suitable quaternary compounds of the formula III are tetrapropylammonium chloride, tetrapropylammonium bromide and tetrapropylammonium iodide, tetrabutylammonium chloride, tetrabutylammonium bromide and tetrabutylammonium iodide, tetrabutylammonium bisulfate, benzyltrimethylammonium chloride, benzyltriethylammonium chloride, benzyltributylammonium iodide, tripropylbutylammonium iodide, tripropylbutylammonium bromide, tributylmethylammonium chloride, tributylmethylammonium iodide, trioctylmethylammonium iodide, trioctylmethylammonium bisulfate, phenyltrimethylammonium chloride or phenyltrimethylammonium bromide, phenyltriethylammonium chloride, tricaprylmethylammonium chloride, decyltrimethylammonium chloride, dodecyltrimethylammonium chloride, hexadecyltrimethylammonium chloride, hexadecylpyridinium chloride, dodecylpyridinium bromide, octylpyridinium bromide, tetrabutylphosphonium chloride, tetrabutylphosphonium bromide and tetrabutylphosphonium iodide, benzyltrimethylphosphonium chloride, benzyltributylphosphonium chloride, tributylmethylphosphonium chloride, trioctylmethylphosphonium bromide, hexadecyltributylphosphonium bromide, decyltributylammonium chloride, dodecyltriethylammonium bromide, tetraphenylphosphonium bromide, hexadecyltrimethylphosphonium bromide, tributylmethylphosphonium iodide and tetraphenylphosphonium bromide. Tetrabutylammonium iodide is a particularly suitable quaternary compound of the formula III.

The 2,6-dialkylaniline of the formula IV, which according to the invention is to be used in excess, is advantageously used in amounts of 1.5–2.5 mols per mol of 2-chloropropionic acid ester of the formula II originally employed. The use of a smaller or larger excess of 2,6-dialkylaniline of the formula IV is possible, but the reaction mixture is difficult to handle if less than 1.5 mols of 2,6-dialkylaniline of the formula IV are used per mol of 2-chloropropionic acid ester of the formula II originally employed, whilst the use of more than 2.5 mols of 2,6-dialkylaniline of the formula IV per mol of 2-chloropropionic acid ester of the formula II originally employed is uneconomical in view of the effort associated with the removal of the excess 2,6-dialkylaniline by distillation. Preferably, 1.6–1.8 mols of 2,6-dialkylaniline of the formula IV are used per mol of 2-chloropropionic acid ester of the formula II originally employed.

According to the invention, suitable acid-binding agents are alkali metal carbonates and alkali metal bicarbonates, such as lithium carbonate, sodium carbonate, potassium carbonate, rubidium carbonate and caesium carbonate, and also lithium bicarbonate, sodium bicarbonate, potassium bicarbonate, rubidium bicarbonate and caesium bicarbonate. Preferred acid-binding agents are sodium carbonate, potassium carbonate, sodium bicarbonate, and potassium bicarbonate. As a rule, the acid-binding agents are employed in approximately the stoichiometric amount or in excess. Advantageously, the acid-binding agents are used in an amount of 1–3 equivalents, based on the hydrogen halide to be bonded. Preferably, 1.1–1.3 equivalents of acid-binding agent are used, based on the hydrogen halide to be bonded.

Within the indicated temperature range of 110°–130° C., in which the reaction of the 2,6-dialkylaniline of the formula IV with the mixture of the 2-chloropropionic acid ester of the formula II and the corresponding 2-iodopropionic acid ester is carried out, temperatures of 115°–125° C. are preferred. The water formed during the reaction of a 2,6-dialkylaniline of the formula IV with the mixture of the 2-chloropropionic acid ester of the formula II and the corresponding 2-iodopropionic acid ester in the presence of an alkali metal carbonate or alkali metal bicarbonate is advantageously separated off during the reaction, by azeotropic distillation. The removal of the water as an azeotrope is advantageously carried out under reduced pressure.

After the reaction has ended, the reaction mixture is cooled and freed from salts by extraction with water. The excess 2,6-dialkylaniline of the formula IV is then separated off from the organic phase by distillation. The removal of the 2,6-dialkylaniline of the formula IV by distillation is advantageously effected in vacuo. The N-(1'-alkoxycarbonylethyl)-2,6-dialkylaniline of the formula I, which is obtained as the residue, can as a rule be used in this form for further reactions, for example for the reaction with carboxylic acid chlorides mentioned initially. However, the product can also be purified by vacuum rectification if this is required for a specific application.

According to the invention, the aqueous extract which is obtained after extracting the reaction mixture with water and which contains all of the alkali metal iodide originally employed is reacted, after adding the corresponding amount of quaternary compound of the formula III, with fresh 2-chloropropionic acid ester of the formula II. In this way, iodine losses can be substantially avoided.

According to a preferred embodiment of the process according to the invention, a 2-chloropropionic acid ester of the formula II is reacted in the presence of water and 1–3% by weight of tetrabutylammonium iodide, based on the 2-chloropropionic acid ester of the formula II employed, with 0.45-0.55 mol of sodium iodide or potassium iodide, per mol of 2-chloropropionic acid ester of the formula II, to give a mixture of the 2-chloropropionic acid ester of the formula II and the corresponding 2-iodopropionic acid ester, and, after separating off the aqueous phase, this mixture is allowed to react at 115°-125° C. in the presence of 0.55 mol of sodium carbonate per mol of 2-chloropropionic acid ester of the formula II originally employed, with 1.7 mols of 2,6-dialkylaniline of the formula IV, the reaction mixture is extracted with water and the mixture of 2,6-dialkylaniline of the formula IV and N-(1'-alkoxycarbonylethyl)-2,6-dialkylaniline of the formula I, which is obtained after separating off the aqueous extract, is separated by distillation. In particular, 2,6-dimethylaniline and methyl 2-chloropropionate can be reacted advantageously in accordance with this preferred embodiment.

Using the process according to the invention, it is possible to prepare the N-(1'-alkoxycarbonylethyl)-2,6-dialkylanilines of the formula I in higher yields and in better quality than with the processes disclosed hitherto. The process according to the invention can be carried out in a simple manner in conventional equipment and is particularly suitable for continuous operation. In view of the high yield and quality of the process products, the low expenditure on apparatus and the fact that losses of expensive iodide can be restricted to a minimum by the re-use of the alkali metal iodide obtained as a by-product, the process according to the invention can be regarded as being particularly economical. Compared with known processes, the process according to the invention also offers ecological advantages, since, because of the high selectivity and the high yield, only very small amounts of decomposition products and by-products pass into the effluent.

The process according to the invention as illustrated in more detail by the example which follows.

EXAMPLE

Preparation of N-(1'-methoxycarbonylethyl)-2,6-dimethylaniline

A mixture of 180.0 g (1.2 mols) of sodium iodide, 245.0 g (2.0 mols) of methyl 2-chloropropionate, 5.0 g of tetrabutylammonium iodide and 400 g of water is stirred under reflux for 3 hours. After cooling to room temperature and separating the phases, 320 g of organic phase and 489 g of aqueous phase are obtained. The organic phase, which contains 45 mol % of methyl 2-chloropropionate and 55 mol % of methyl 2-iodopropionate as well as the tetrabutylammonium iodide, is heated, after adding 411.0 g (3.4 mols) of 2,6-dimethylaniline and 115.0 g (1.08 mol) of sodium carbonate, to 105° C., with stirring, and is kept at this temperature for 7 hours. The reaction mixture is then cooled to 25° C. and extracted with 400 g of water. After adding 5.0 g of tetrabutylammonium iodide, the resulting aqueous extract is used for reaction with further methyl 2-chloropropionate. The organic phase (580 g) is worked up by distillation. 190.0 g of 2,6-dimethylaniline and 362.0 g (95.7% of theory, based on the 2,6-dimethylaniline converted) of N-(1'-methoxycarbonylethyl)-2,6-dimethylaniline are obtained.

What is claimed is:

1. A process for the preparation of N-(1'-alkoxycarbonylethyl)-2,6-dialkylanilines of the formula I

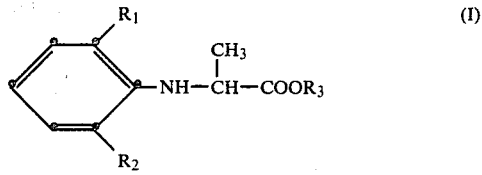

in which $R_1$ and $R_2$ are each methyl or ethyl and $R_3$ is an alkyl group having 1-4 carbon atoms, which comprises reacting a 2-chloropropionic acid ester of the formula II

in which $R_3$ is as defined above, in the presence of water and of a quaternary compound of the formula III

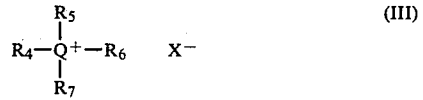

in which Q is nitrogen or phosphorus, the radicals $R_4$, $R_5$, $R_6$ and $R_7$ are each an alkyl radical having 1 to 16 carbon atoms, or phenyl, and one of the radicals $R_4$, $R_5$, $R_6$ and $R_7$ can also be benzyl, and, if Q is nitrogen, Q together with three of the radicals $R_4$, $R_5$, $R_6$ and $R_7$ can also be a pyridine radical, whilst the fourth radical is alkyl having 1-16 carbon atoms, phenyl or benzyl, and $X^\ominus$ is a halide anion or a bisulfate anion, with an alkali metal iodide to give a mixture of the 2-chloropropionic acid ester of the formula II and the corresponding 2-iodopropionic acid ester, subsequently reacting this mixture, after separating off the aqueous phase, at 100°-130° C., in the presence of an alkali metal carbonate or alkali metal bicarbonate as an acid acceptor, with excess 2,6-dialkylaniline of the formula IV

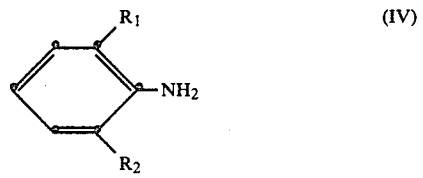

in which $R_1$ and $R_2$ are as defined, extracting the reaction mixture with water and separating, by distillation, the mixture of 2,6-dialkylaniline of the formula IV and N-(1'-alkoxycarbonylethyl)-2,6-dialkylaniline of the formula I, which is obtained after separating off the aqueous extract.

2. A process according to claim 1, wherein the alkali metal iodide is employed in an amount of 0.3-0.6 mol per mol of 2-chloropropionic acid ester of the formula II.

3. A process according to claim 1, wherein the alkali metal iodide is employed in an amount of 0.45-0.55 mol per mol of 2-chloropropionic acid ester of the formula II.

4. A process according to claim 1, wherein the alkali metal iodide used is sodium iodide or potassium iodide.

5. A process according to claim 1, wherein the quaternary compound of the formula III is used in an amount of 0.5–5.0% by weight, based on the 2-chloropropionic acid ester of the formula II employed.

6. A process according to claim 1, wherein the quaternary compound of the formula III is used in an amount of 1–3% by weight, based on the 2-chloropropionic acid ester of the formula II employed.

7. A process according to claim 1, wherein the quaternary compound of the formula III which is used is tertrabutylammonium iodide.

8. A process according to claim 1, wherein the 2,6-dialkylaniline of the formula IV is used in amounts of 1.5–2.5 mols per mol of 2-chloropropionic acid ester originally employed.

9. A process according to claim 1, wherein the 2,6-dialkylaniline of the formula IV is used in an amount of 1.6–1.8 mols per mol of 2-chloropropionic acid ester originally employed.

10. A process according to claim 1, wherein the acid-binding agent is used in an amount of 1–3 equivalents, based on the hydrogen halide to be bonded.

11. A process according to claim 1, wherein the 1.1–1.3 equivalents of acid-binding agent are used, based on the hydrogen halide to be bonded.

12. A process according to claim 1, wherein the reaction of a 2,6-dialkylaniline of the formula IV with the mixture of the 2-chloropropionic acid ester of the formula II and the corresponding 2-iodopropionic acid ester is carried out at a temperature of 115°–120° C.

13. A process according to claim 1, wherein the aqueous extract obtained after reacting a mixture of the 2-chloropropionic acid ester of the formula II and the corresponding 2-iodopropionic acid ester with a 2,6-dialkylaniline of the formula IV and extracting the reaction mixture with water is used, after the addition of a quaternary compound of the formula III, for reaction with a 2-chloropropionic acid ester of the formula II.

14. A process according to claim 1, wherein a 2-chloropropionic acid ester of the formula II is reacted in the presence of water and 1–3% by weight of tetrabutylammonium iodide, based on 2-chloropropionic acid ester of the formula II employed, with 0.45–0.55 mol of sodium iodide or potassium iodide per mol of 2-chloropropionic acid ester of the formula II to give a mixture of the 2-chloropropionic acid ester of the formula II and the corresponding 2-iodopropionic acid ester, and, after separating off the aqueous phase, this mixture is allowed to react, at 115°–120° C., in the presence of 0.55 mol of sodium carbonate per mol of 2-chloropropionic acid ester of the formula II originally employed, with 1.7 mols of a 2,6-dialkylaniline of the formula IV, per mol of 2-chloropropionic acid ester of the formula II originally employed, the reaction mixture is extracted with water and the mixture of the 2,6-dialkylaniline of the formula IV and the N-(1'-alkoxycarbonylethyl)-2,6-dialkylaniline of the formula I, which is obtained after separating off the aqueous extract, is separated by distillation.

15. A process according to claim 1, wherein the 2,6-dialkylaniline of the formula IV which is used is 2,6-dimethylaniline.

16. A process according to claim 1, wherein the 2-chloropropionic acid ester of the formula II which is used is methyl 2-chloropropionate.

* * * * *